US010446375B2

(12) United States Patent
Egawa

(10) Patent No.: US 10,446,375 B2
(45) Date of Patent: Oct. 15, 2019

(54) LIQUID PROCESSING APPARATUS INCLUDING CONTAINER, FIRST AND SECOND ELECTRODES, INSULATOR SURROUNDING AT LEAST PART OF SIDE FACE OF THE FIRST ELECTRODE, GAS SUPPLY DEVICE, METALLIC MEMBER SURROUNDING PART OF SIDE FACE OF THE FIRST ELECTRODE, AND POWER SOURCE

(71) Applicant: Panasonic Intellectual Property Management Co., Ltd., Osaka (JP)

(72) Inventor: Minoru Egawa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 95 days.

(21) Appl. No.: 15/900,994

(22) Filed: Feb. 21, 2018

(65) Prior Publication Data
US 2018/0269040 A1 Sep. 20, 2018

(30) Foreign Application Priority Data
Mar. 14, 2017 (JP) .................. 2017-049098

(51) Int. Cl.
*H01J 37/32* (2006.01)
*C02F 1/46* (2006.01)
(Continued)

(52) U.S. Cl.
CPC .......... *H01J 37/32807* (2013.01); *A61L 2/14* (2013.01); *B01J 19/088* (2013.01); *C02F 1/4608* (2013.01);
(Continued)

(58) Field of Classification Search
CPC ............. C02F 1/4608; C02F 2305/023; C02F 2301/043; C02F 2301/046; C02F 2303/04;
(Continued)

(56) References Cited

U.S. PATENT DOCUMENTS

| 5,316,739 A | 5/1994 | Yoshikawa et al. |
| 2014/0174359 A1 | 6/2014 | Tabata et al. |
| 2014/0231329 A1 | 8/2014 | Imai et al. |

FOREIGN PATENT DOCUMENTS

| JP | 6-065739 | 3/1994 |
| JP | 2007-181294 | 7/2007 |

(Continued)

*Primary Examiner* — Lessanework Seifu
(74) *Attorney, Agent, or Firm* — McDermott Will & Emery

(57) ABSTRACT

A liquid processing apparatus includes a container for holding liquid, a first electrode, a second electrode, a first insulator that has a cylindrical shape and at least partly surrounds a side face of the first electrode via a space, the first insulator having an opening in an end face of the first insulator, a gas supply device that supplies gas into the space and releases the gas into the liquid via the opening, a power source that applies a voltage between the first electrode and the second electrode and generates plasma, and a metallic member that partly surrounds the side face of the first electrode via the space. The metallic member is electrically connected to the first electrode. At least a part of the first insulator is disposed between the first electrode and the metallic member.

18 Claims, 12 Drawing Sheets

(51) Int. Cl.
  *A61L 2/14* (2006.01)
  *B01J 19/08* (2006.01)
  *C02F 1/461* (2006.01)

(52) U.S. Cl.
  CPC .... *H01J 37/3244* (2013.01); *H01J 37/32541* (2013.01); *H01J 37/32761* (2013.01); *C02F 2001/46171* (2013.01); *C02F 2201/003* (2013.01); *C02F 2301/043* (2013.01); *C02F 2301/046* (2013.01); *C02F 2303/04* (2013.01); *C02F 2305/023* (2013.01); *H01J 2237/038* (2013.01)

(58) Field of Classification Search
  CPC ............. H01J 37/32807; H01J 37/3244; H01J 37/32541; H01J 37/32761; H01J 2237/038; A61L 12/14; B01J 19/088
  See application file for complete search history.

(56) References Cited

FOREIGN PATENT DOCUMENTS

| | | |
|---|---|---|
| JP | 2010-141194 | 6/2010 |
| JP | 2012-101140 | 5/2012 |
| JP | 2014-159010 | 9/2014 |
| JP | 2015-033694 | 2/2015 |
| JP | 2015-136644 | 7/2015 |
| JP | 2016-106359 | 6/2016 |
| WO | 2013/035375 | 3/2013 |

LIQUID PROCESSING APPARATUS INCLUDING CONTAINER, FIRST AND SECOND ELECTRODES, INSULATOR SURROUNDING AT LEAST PART OF SIDE FACE OF THE FIRST ELECTRODE, GAS SUPPLY DEVICE, METALLIC MEMBER SURROUNDING PART OF SIDE FACE OF THE FIRST ELECTRODE, AND POWER SOURCE

BACKGROUND

1. Technical Field

The present disclosure relates to a liquid processing apparatus.

2. Description of the Related Art

Japanese Unexamined Patent Application Publication No. 2015-33694 discloses a liquid processing apparatus that can be used in the decomposition of the bacteria by generating plasma in bubbles produced in water and sending reactive species such as OH radicals into the water. The liquid processing apparatus disclosed in Japanese Unexamined Patent Application Publication No. 2015-33694 sends a current of gas through an opening of an insulator in order to produce bubbles in water, applies a high voltage between a first electrode disposed inside the insulator and a second electrode disposed in the water, and generates plasma in the bubbles.

SUMMARY

In one general aspect, the techniques disclosed here feature a liquid processing apparatus including: a container for holding liquid; a first electrode at least a part of which is disposed in the liquid; a second electrode at least a part of which is disposed in the liquid; a first insulator that has a cylindrical shape and at least partly surrounds a side face of the first electrode via a space, the first insulator having an opening in an end face of the first insulator; a gas supply device that supplies gas into the space and releases the gas into the liquid via the opening; a power source that applies a voltage between the first electrode and the second electrode and generates plasma; and a metallic member that partly surrounds the side face of the first electrode via the space. The metallic member is electrically connected to the first electrode. At least a part of the first insulator is disposed between the first electrode and the metallic member.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Brief Overview of the Present Disclosure

Figure 1:
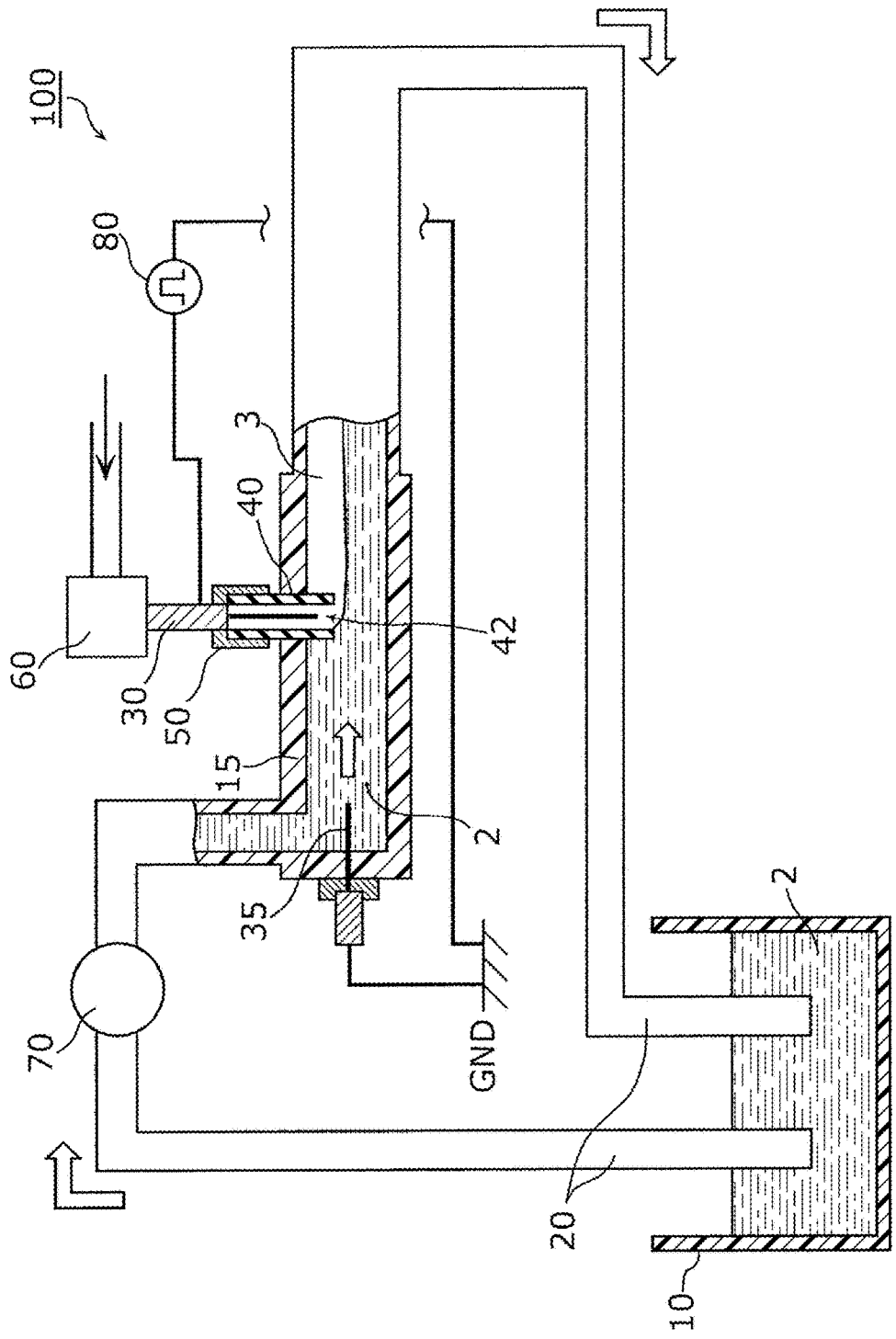
FIG. 1 is a diagram showing a configuration of a liquid processing apparatus according to an embodiment of the present disclosure.

In one general aspect, the techniques disclosed here feature a liquid processing apparatus including: a container for holding liquid; a first electrode at least a part of which is disposed in the liquid; a second electrode at least a part of which is disposed in the liquid; a first insulator that has a cylindrical shape and at least partly surrounds a side face of the first electrode via a space, the first insulator having an opening in an end face of the first insulator; a gas supply device that supplies gas into the space and releases the gas into the liquid via the opening; a power source that applies a voltage between the first electrode and the second electrode and generates plasma; and a metallic member that partly surrounds the side face of the first electrode via the space. The metallic member is electrically connected to the first electrode. At least a part of the first insulator is disposed between the first electrode and the metallic member.

The first electrode may have a first end and a second end located closer to the liquid than the first end, and the metallic member may not surround a portion of the side face of the first electrode, the portion extending from the second end to a position between the first end and the second end.

Further, a potential of the metallic member may become substantially the same as a potential of the first electrode when the voltage is applied between the first electrode and the second electrode.

This makes it possible to attain an electric field strength of substantially 0 inside a part of the first insulator surrounded by the metallic member, thus making it possible to reduce the force with which the liquid is drawn to a back side of the first insulator under Maxwell stress induced by an electric field. That is, this makes it possible to prevent the entrance of the liquid into a back part of the first insulator.

This in turn makes it possible to prevent a decrease in discharge efficiency in a desired place from occurring due to discharge in the back part of the first insulator. This also makes it possible to prevent a member holding the insulator or a similar member from burning out due to discharge in the back part of the first insulator. This makes it possible to maintain the performance of the liquid processing apparatus over a long period of time and contribute to safety and security.

Further, the first insulator may be disposed between the first electrode and the metallic member. This makes it only necessary to dispose the metallic member around the first insulator, thus making it possible to prevent the entrance of the liquid into the back part of the first insulator with a simple configuration. For example, this makes it possible to utilize an existing insulator, an existing electrode, and the like, thus making it possible to reduce cost.

It should be noted that there is a risk that Maxwell stress may cause the liquid to enter that part of an interior space of the first insulator which extends from the opening and which is not surrounded by the metallic member. Specifically, there is a risk that the liquid may enter through the opening up to an end of the metallic member that faces the opening in an axial direction of the first insulator.

A part of the first electrode surrounded by the space has two ends. One end of the two ends is located farther away from the opening than the other end of the two ends. The metallic member may surround a portion of the side face of the first electrode, the portion extending from the one end to a position that is located at a distance of 10 mm or longer from the one end.

With this, a front end of the metallic member 50 corresponding to the part that the liquid may enter and a base portion of the first electrode can be placed at a distance of 10 mm or longer from each other. This makes it possible to prevent the occurrence of a dielectric breakdown in the presence of the application of a voltage of 5 kV.

Further, the metallic member may be in contact with an outer side face of the first insulator.

This brings the metallic member and the first electrode closer to each other, thus making it possible to further weaken the electric field intensity inside the first insulator surrounded by the metallic member. This makes it possible to further prevent the entrance of the liquid into the back part of the first insulator.

Further, the liquid processing apparatus may further include a second insulator covering at least a part of the metallic member.

This makes it possible to prevent discharge at the desired place from being precluded by contact between a high-potential metallic member and a grounded liquid. This also makes it possible to prevent the occurrence of a short circuit.

Further, the metallic member may be buried in the first insulator.

This makes it possible to prevent discharge at the desired place from being precluded by contact between a high-potential metallic member and a grounded liquid. This also makes it possible to prevent the occurrence of a short circuit.

Further, the first insulator may include a first portion and a second portion, the metallic member may be disposed between the first portion and the second portion, and the second portion may be disposed between the metallic member and the first electrode.

This makes it possible to prevent the entrance of the liquid under Maxwell stress. This further eliminates the need to provide an outer part of the first insulator with a metallic member and an insulator that protects the metallic member.

This makes it possible to miniaturize the liquid processing apparatus with a space-saving configuration.

Further, the first and second portions of the first insulator may be made of different materials from each other.

This makes it possible to vary a parameter such as a dielectric constant, breakdown voltage, or workability according to location, thus making it possible to contribute to miniaturization of the liquid processing apparatus and lowering of a level of difficulty in manufacturing while maintaining performance.

Further, the first and second portions of the first insulator may be made of the same material.

This makes it possible to reduce the number of manufacturing steps, thus making it possible to reduce cost.

Further, the metallic member may have a cylindrical shape.

This prevents leakage of an electric field from a place surrounded by the metallic member, thus making it possible to strongly shield an electric field.

Further, the metallic member may have a cylindrical mesh shape, a spiral shape, or a shape of a plurality of metallic rods annularly arrayed at pitches.

In this case, for example, the widths of openings of the mesh shape, the pitches between spirals of the spiral shape, or the pitches between the plurality of metallic rods may be shorter than or equal to the distance between the first insulator and the first electrode.

With this, in such a repressed state that leakage of an electric field does not take place, the drawing of the liquid by an electric field can be prevented. This also makes it possible to reduce the amount of the metallic member, thus making it possible to achieve reductions in weight and cost of the liquid processing apparatus.

Further, the first electrode may include an electrode section having a circular columnar shape, the first insulator may be a circular cylinder surrounding a part of a side face of the electrode section, and the electrode section and the first insulator may be coaxially disposed.

The coaxial disposition of circular cylindrical shapes makes it possible to suppress a deviation of an electric potential distribution, thus making it possible to effectively prevent the entrance of the liquid into the back part of the first insulator.

The following describes an embodiment in concrete terms with reference to the drawings.

It should be noted that the embodiment to be described below shows a general or specific example. The numerical values, the shapes, the materials, the constituent elements, the placement location and connection configuration of the constituent elements, the steps, the order of the steps, and the like that are shown in the following embodiment are mere examples and are not intended to limit the present disclosure. Further, those of the constituent elements in the following embodiment which are not recited in an independent claim representing the most generic concept are described as optional constituent elements.

Further, each drawing is a schematic diagram and is not necessarily strictly illustrated. Therefore, each drawing does not necessarily agree in scale or the like to the other drawing. Further, each drawing gives the same reference numerals to substantially the same components so that a repeated description may be omitted or simplified.

Further, terms such as "parallel" or "perpendicular" used to describe a relationship between elements, terms such as "circular column" used to describe the shape of an element, the ranges of numerical values, and similar expressions are herein not expressions with rigorous meanings only but expressions meant to encompass substantially equal ranges, e.g. differences of approximately several percent.

Embodiment

The following describes an embodiment with reference to the drawings.

1. Brief Overview

First, a brief overview of a liquid processing apparatus 100 according to an embodiment is given with reference to FIG. 1. FIG. 1 is a diagram showing a configuration of the liquid processing apparatus 100 according to the present embodiment. It should be noted that FIG. 1 shows an example of a cross-sectional configuration of a processing tank 10 in which a processed liquid 2 is stored, a reaction tank 15 in which plasma processing is performed on the processed liquid 2, and the area therearound and schematically shows other components such as a piping unit 20 and a gas supply device 60.

As shown in FIG. 1, the liquid processing apparatus 100 generates plasma in gas 3 supplied into the processed liquid 2. The gas 3 supplied into the processed liquid 2 is present as bubbles in the processed liquid 2.

The processed liquid 2 is a liquid such as water, for example pure water, tap water, or waste water. The liquid processing apparatus 100 applies a voltage between a first electrode 30 and a second electrode 35 and generates plasma in the gas 3 supplied to the processed liquid 2. This causes active species such as OH radicals or nitrogen oxides to be produced and sent into the water, thereby making it possible to sterilize the processed liquid 2 per se or decompose an organic substance. Alternatively, the processed liquid 2 may be made by plasma processing to contain active species to be used for various purposes such as the sterilization of another gas or liquid or the decomposition of an organic substance in another gas or liquid and the eradication of the bacteria having adhered to another substance or the decomposition of an organic substance having adhered to another substance. It should be noted that examples of active species include hydroxyl radicals (OH), hydrogen radicals (H), oxygen radicals (O), superoxide anions ($O^{2-}$), monovalent oxygen ions ($O^-$), and hydrogen peroxide ($H_2O_2$).

2. Configuration

Next, the configuration of the liquid processing apparatus 100 according to the present embodiment is described.

Figure 2:
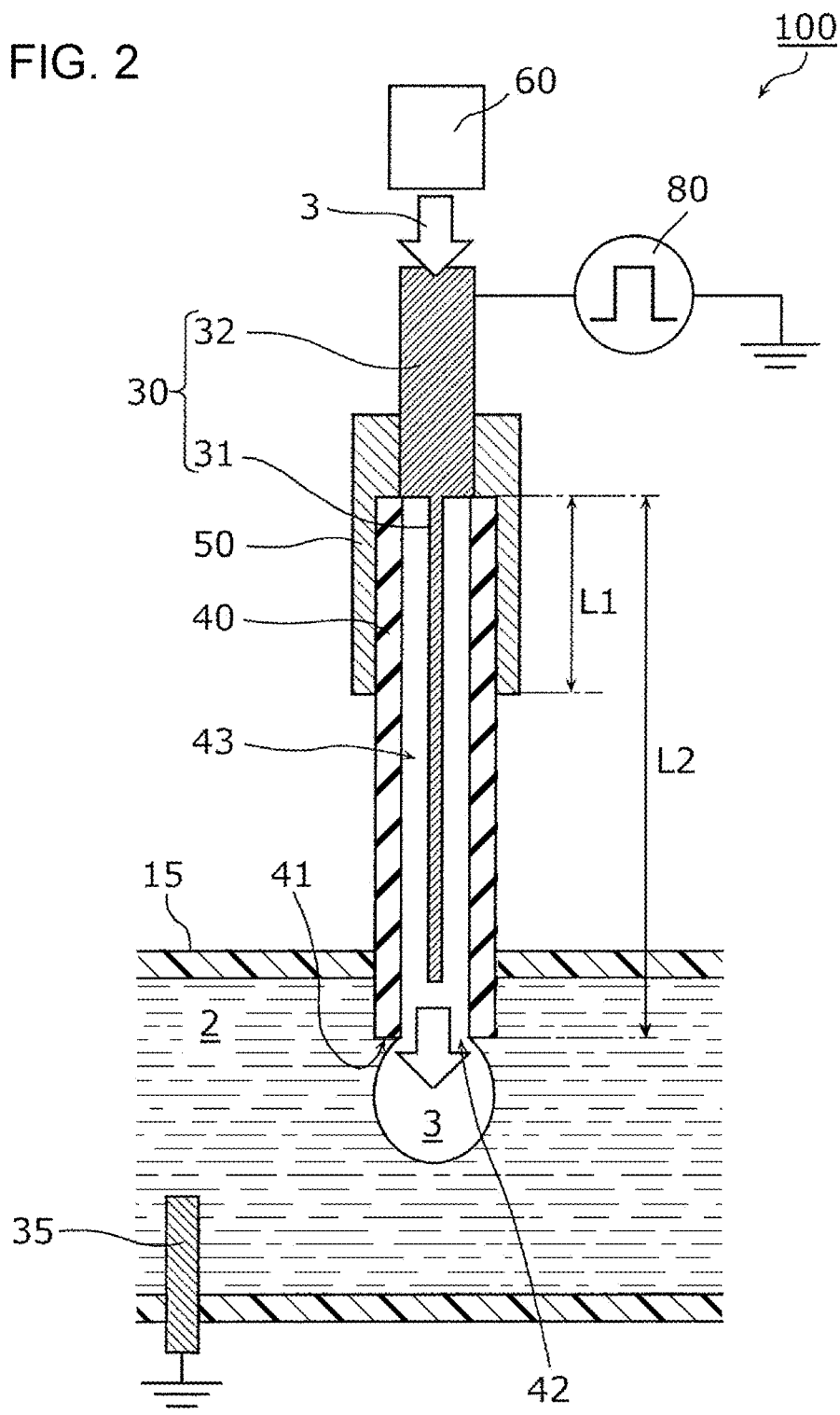
FIG. 2 is a cross-sectional view showing an example of a configuration of the main components of the liquid processing apparatus according to the embodiment.

As shown in FIG. 1, the liquid processing apparatus 100 includes the processing tank 10, the reaction tank 15, the piping unit 20, the first electrode 30, the second electrode 35, an insulator 40, a metallic member 50, the gas supply device 60, a liquid supply device 70, and a power source 80. The following uses FIG. 2 to describe each of the constituent elements of the liquid processing apparatus 100 in detail with appropriate reference to FIG. 1. FIG. 2 is a cross-sectional view showing a configuration of the main components of the liquid processing apparatus 100 according to the present embodiment.

2-1. Processing Tank

The processing tank 10 is a container for storing the processed liquid 2. The processing tank 10 may have any outer shape such as a rectangular parallelepiped, a circular cylinder, or a sphere. An example of the processing tank 10 is an upwardly open tray.

To the processing tank 10, the piping unit 20 is connected. Specifically, the processing tank 10 is connected to the reaction tank 15 via the piping unit 20. To the piping unit 20, the liquid supply device 70 is connected so that the processed liquid 2 circulates among the processing tank 10, the reaction tank 15, and the piping unit 20.

The processing tank 10 is made, for example, of an acid-resistant resinous material or a similar material. For example, the processing tank 10 is made of fluororesin such as polytetrafluoroethylene, silicon rubber, polyvinyl chloride, stainless steel, or ceramic.

2-2. Reaction Tank

The reaction tank 15 is a tank inside which at least a part of each of the first and second electrodes 30 and 35 is disposed. Specifically, the first electrode 30 and the second electrode 35 are disposed so as to penetrate through side walls of the reaction tank 15.

The reaction tank 15 contains a flow passage through which the processed liquid 2 flows. The flow passage is filled with the processed liquid 2. At least the part of each of the first and second electrodes 30 and 35 is disposed in the flow passage. Into the flow passage, the gas 3 supplied by the gas supply device 60 is released as bubbles via an opening 42 of the insulator 40. Discharge between the first electrode 30 and the second electrode 35 causes plasma to be generated in the gas 3.

An example of the reaction tank 15 is, but is not limited to, a rectangular or circular cylindrical container elongated in a horizontal direction. An example of the reaction tank 15 may be an enclosed liquid storage tank or an upwardly open tray. Alternatively, the reaction tank 15 may be a part of the piping unit 20.

The reaction tank 15 is made, for example, of an acid-resistant resinous material or a similar material. For example, the reaction tank 15 is made of fluororesin such as polytetrafluoroethylene, silicon rubber, polyvinyl chloride, stainless steel, or ceramic.

2-3. Piping Unit

The piping unit 20 is a pipe that forms a circulatory pathway of the processed liquid 2. The piping unit 20 is formed by a tubular member such as a pipe, a tube, or a hose. The piping unit 20 is made of an acid-resistant resinous or metallic material or a similar material. For example, the piping unit 20 is made of fluororesin such as polytetrafluoroethylene, silicon rubber, polyvinyl chloride, stainless steel, or ceramic.

In the present embodiment, the piping unit 20 connects the processing tank 10 to the liquid supply device 70, connects the liquid supply device 70 to the reaction tank 15, and connects the reaction tank 15 to the processing tank 10. In this way, the piping unit 20 forms the circulatory pathway of the processed liquid 2 by connecting the processing tank 10 to the liquid supply device 70, connecting the liquid supply device 70 to the reaction tank 15, and connecting the reaction tank 15 to the processing tank 10.

2-4. First Electrode

The first electrode 30 is one of the pair of electrodes for generating plasma. The first electrode 30 is used as a reaction electrode around which plasma is generated. The first electrode 30 functions as an anode. As shown in FIG. 2, the first electrode 30 includes an electrode section 31 and a supporting section 32. The first electrode 30 has a first end and a second end located closer to the processed liquid 2 than the first end.

The electrode section 31 is an elongated circular columnar electrode section and a portion of the first electrode 30 that faces a front-end side. It should be noted that the term "front-end side" refers to a direction toward an end face 41 of the insulator 40 and the opening 42. To the supporting section 32, which is on a back-end side opposite to the front-end side, the gas supply device 60 is connected. This allows the gas 3 to flow along the electrode section 31 toward the front end.

Plasma is generated between the front end of the electrode section 31 and a gas-liquid interface between the gas 3 covering the front end and the processed liquid 2. It should be noted that the front end of the electrode section 31 is on a further back side than the opening 42 of the insulator 40 by an amount corresponding to the distance between the front end of the electrode section 30 and the end face 41 of the insulator 40 that touches the processed liquid 2. For example, the amount is 3 mm or shorter. An example of the amount is 2 mm.

The electrode section 31 is for example 1 mm in diameter and 40 mm in length. It should be noted that the shape of the electrode section 31 is not limited to this shape but may be any shape such as a shape formed by connecting a sphere to the front end of a triangular prism, an elliptic column, or a circular column. Further, the electrode section 31 does not need to be straight but may be curved.

The electrode section 31 is made, for example, of tungsten, tungsten yttrium, or a similar material. A material such as tungsten or tungsten yttrium has high resistance to plasma and hardly suffers from electrode wear. Alternatively, the electrode section 31 may be made, for example, of copper or iron. In a case where the electrode section 31 is made of copper or iron, hydrogen peroxide produced by a recombination of OH radicals and copper ions or iron ions react so that OH radicals can be produced again to improve capabilities such as sterilization or organic matter decomposition.

The supporting section 32 is a member made of metal that supports the electrode section 31. Specifically, the electrode section 31 is fixed by being press fitted into the supporting section 32. The supporting section 32 is electrically connected to the electrode section 31 and transmits electric power received from the power source 80 to the electrode section 31.

The supporting section 32 is a circular columnar portion of the first electrode 30 that is provided on the back-end side. The supporting section 32 is larger in diameter than the electrode section 31 and, for example, is the same in size as the opening 42 of the insulator 40. The supporting section 32 is made of an easily-workable metallic material such as iron.

It should be noted that, although not illustrated, the supporting section 32 has a through-hole through which the gas 3 flows. The through-hole extends along an axial direction. To the back-end side of the supporting section 32, the gas supply device 60 is connected so that the gas 3 is supplied to a space 43 via the through-hole. The space 43 is an interior space of the insulator 40.

It should be noted that the electrode section 31 and the supporting section 32 may be integrally formed. For example, the electrode section 31 and the supporting section 32 may be made of the same material. The electrode section 31 and the supporting section 32 are not particularly limited in shape.

2-5. Second Electrode

The second electrode 35 is the other one of the pair of electrodes for generating plasma. The second electrode 35 functions as a cathode. At least the part of the second electrode 35 is disposed in the flow passage of the reaction tank 15. The second electrode 35 is in contact with the processed liquid 2.

Although, in the present embodiment, the second electrode 35 is disposed in the flow passage upstream of the first electrode 30 as shown in FIG. 1, this does not imply any limitation. The second electrode 35 may alternatively be disposed in the flow passage downstream of the first electrode 30. Further, the second electrode 35 may be disposed in a location opposite to the first electrode 30 so as to be orthogonal to the direction in which the processed liquid 2 flows.

The second electrode 35 is for example identical, but may be different, in size, material, and the like to the first electrode 30. For example, the second electrode 35 may be made of platinum, titanium coated with platinum, or a similar material.

2-6. Insulator

The insulator 40 is an example of a cylindrical first insulator disposed so as to surround a side face of the first electrode 30 via the space 43 and provided with the opening 42 in the end face 41 that touches the processed liquid 2. In the present embodiment, the insulator 40 is disposed between the first electrode 30 and the metallic member 50. Specifically, the insulator 40 is an elongated cylinder disposed between the electrode section 31 of the first electrode 30 and the metallic member 50 so as to surround a side face of the electrode section 31. It should be noted that the shape of the insulator 40 is for example a circular cylinder but may alternatively be any shape such as a triangular cylinder or an elliptical cylinder.

The inner diameter of the insulator 40 is larger than the outer diameter of the electrode section 31. Further, the electrode section 31 and the insulator 40 are coaxially disposed. For this reason, the space 43 is formed in a circular cylindrical shape over the entire perimeter of the side face of the electrode section 31. The space 43 keeps the electrode section 31 out of contact with the insulator 40. The insulator 40 is for example 3 mm in inner diameter and 4 mm in outer diameter.

The insulator 40 is composed, for example, of ceramic such as alumina. Alternatively, the insulator 40 may be made of magnesia, zirconia, quartz, yttrium oxide, or a similar material.

For example, as shown in FIGS. 1 and 2, the insulator 40 is fixed so as to penetrate through a wall surface of the reaction tank 15 so that the opening 42 touches the processed liquid 2. It should be noted that a watertight member such as packing may be provided to fill a boundary division between the insulator 40 and the reaction tank 15.

2-7. Metallic Member

The metallic member 50 surrounds, via the space 43, a part of the side face of the first electrode 30 excluding a part of the side face of the first electrode 30 extending from the front end of the first electrode 30 over a predetermined distance toward the back end of the first electrode 30. In other words, the metallic member 50 surrounds, via the space 43, a part of the side face of the first electrode 30 excluding a part of the side face of the first electrode extending from the second end, which is an end of the first electrode 30 located closer to the processed liquid 2, to a predetermined location between the first and second ends of the first electrode 30. In the present embodiment, as shown in FIG. 2, the metallic member 50 is in contact with an outer side face of the insulator 40.

Let it be assumed here that, as shown in FIG. 2, L1 is the axial length over which the metallic member 50 surrounds the side face of the electrode section 31 of the first electrode 30. Further, L2 is the axial length of the insulator 40. In the present embodiment, the length of the space 43, which is an interior space of the insulator 40, is equal to the length of the insulator 40.

As shown in FIG. 2, the metallic member 50 surrounds a portion of the insulator 40 that faces the back-end side of the space 43. Specifically, the metallic member 50 surrounds an area extending from the back end of the space 43 over the distance L1 toward the opening 42. It should be noted that the back end is an end of the space 43 opposite to the opening 42. Meanwhile, the metallic member 50 does not surround the front end of the space 43, i.e. an area extending from the opening 42 over a distance L2−L1.

The distance L1 is for example 10 mm or longer. For example, in a case where the distance L1 is 10 mm, a dielectric breakdown voltage of approximately 10 kV is attained. In a case where the power source 80 supplies a voltage of, for example, 5 kV, a margin of twice as high a voltage is allowed. It should be noted that in a case the power source 80 applies a low voltage, the distance L1 may be shorter than 10 mm. For example, in a case where the power source 80 applies a voltage of 1 kV, the distance L1 may be 2 mm or longer.

The metallic member 50 is made, for example, of stainless steel or, specifically, SUS304. It should be noted that the metallic member 50 may be made of the same material as the first electrode 30. For example, the metallic member 50 may be integrally formed with the first electrode 30.

Further, the metallic member 50 is electrically connected to the first electrode 30 so that the metallic member 50 is at substantially the same potential as the first electrode 30 in the presence of the application of a predetermined voltage by the power source 80. It should be noted that the term "substantially the same potential" encompasses not only a case where the potential of the metallic member 50 and the potential of the first electrode 30 are exactly the same but also a case where the potentials fall within substantially the same range, e.g. a case where there is a difference of several percent between the potentials. For example, the term "substantially the same potential" also encompasses a case where the potentials are out of complete agreement due to the influence of the internal resistances of the first electrode 30 and the metallic member 50, the contact resistance between the first electrode 30 and the metallic member 50, and the like.

Figure 3:
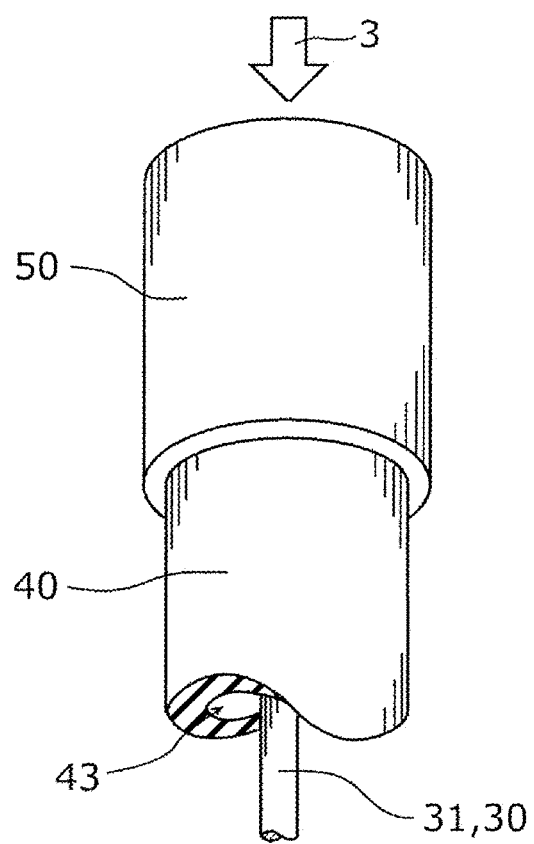
FIG. 3 is a perspective view showing the shape of a metallic member of the liquid processing apparatus according to the embodiment.

In the present embodiment, as shown in FIG. 3, the metallic member 50 has, for example, a cylindrical shape. Specifically, the metallic member 50 is a circular cylinder whose inner diameter is substantially equal to the outer diameter of the insulator 40. It should be noted that FIG. 3 is a perspective view showing the shape of the metallic member 50 of the liquid processing apparatus 100 according to the present embodiment. FIG. 3 is a partially cutaway view of the insulator 40 and the first electrode 30. It should be noted that the shape of the metallic member 50 is not limited to the example shown in FIG. 3. Other modifications of the metallic member 50 will be described later with reference to FIGS. 7 to 10.

2-8. Gas Supply Device

The gas supply device 60 releases the gas into the processed liquid 2 via the opening 42 by supplying the gas 3 to the inside of the insulator 40. For example, the gas supply device 60 is connected to the supporting section 32 of the first electrode 30. For example, the gas supply device 60 takes in ambient air and supplies it as the gas 3 to the space 43 via the through-hole of the supporting section 32.

It should be noted that the gas supply device 60 may supply nitrogen gas, oxygen gas, argon, helium or a similar gas instead of supplying air.

In the present embodiment, the gas supply device 60 supplies the gas 3 at a flow rate of, for example, 0.5 L (liter)/min or higher. An example of the flow rate is 2.0 L/min. The gas 3 supplied by the gas supply device 60 pushes the processed liquid 2 out of the space 43 through the opening 42 and covers the electrode section 31. The gas 3 is released into the processed liquid 2 in the reaction tank 15 via the opening 42.

2-9. Liquid Supply Device

The liquid supply device 70 causes the processed liquid 2 to circulate between the processing tank 10 and the reaction tank 15 via the piping unit 20. In the present embodiment, the liquid supply device 70 is disposed in the middle of the piping unit 20.

2-10. Power Source

The power source 80 generates plasma by applying a predetermined voltage between the first electrode 30 and the second electrode 35. Specifically, the power source 80 applies a pulse voltage or an AC voltage between the first electrode 30 and the second electrode 35.

The voltage that the power source 80 applies is a positive high-voltage pulse of, for example, 2 kV/cm to 50 kV/cm and 1 Hz to 100 kHz. The voltage waveform may for example be a pulse waveform, a semisinusoidal waveform, or a sinusoidal waveform. Further, the value of a current that flows between the first electrode 30 and the second electrode 35 ranges, for example, from 1 mA to 3 A. In this case, the power source 80 applies a pulse voltage, for example, so that the first electrode 30 serves as a positive electrode and the second electrode 35 serves as a negative electrode. The pulse voltage has, for example, a maximum value of 5 kV, a frequency of 30 kHz, and a duty ratio of 50%. Alternatively, a maximum value may be reached only immediately after a rising edge by resonance between the power source 80 and a load, and after that, a constant voltage of approximately 2 kV may be applied.

3. Operation

The following describes in detail how the liquid processing apparatus 100 according to the present embodiment operates.

First, the gas supply device 60 supplies the gas 3 into the processed liquid 2 through the opening 42 of the insulator 40 located in the processed liquid 2. The flow rate of the gas 3 is for example 2.0 L/min. As shown in FIG. 2, the opening 42 of the insulator 40 is covered with the gas 3 released out of the interior space 43. At this point in time, the electrode section 31 of the first electrode 30 is kept out of direct contact with the processed liquid 2 by being covered with the gas 3 (i.e. bubbles) thus supplied. Therefore, the gas 3 covering the opening 42 of the insulator 40 functions as an insulator inserted between the first electrode 30 and the second electrode 35.

While the gas 3 is being supplied, the power source 80 applies a pulse voltage of, for example, 5 kV between the first electrode 30 and the second electrode 35. This causes plasma to be generated in the gas 3 covering the opening 42 of the insulator 40. The plasma contains active species such as OH radicals and NO radicals, and these active species are introduced into the processed liquid 2. The active species react with the bacteria or odorous components in the processed liquid 2 as they are or as reaction products such as nitrate ions or nitrite ions, whereby sterilization or decomposition takes place.

4. Modifications

Modifications according to the present embodiment are described here with reference to FIGS. 4 to 10. The following describes modifications of the insulator 40 and modifications of the metallic member 50. The modifications to be described here are described with attention focused on points of difference from the embodiment with omission or simplification of a description of common points. Unless otherwise noted, the modifications are substantially the same as the embodiment.

4-1. Modification 1

Figure 4:
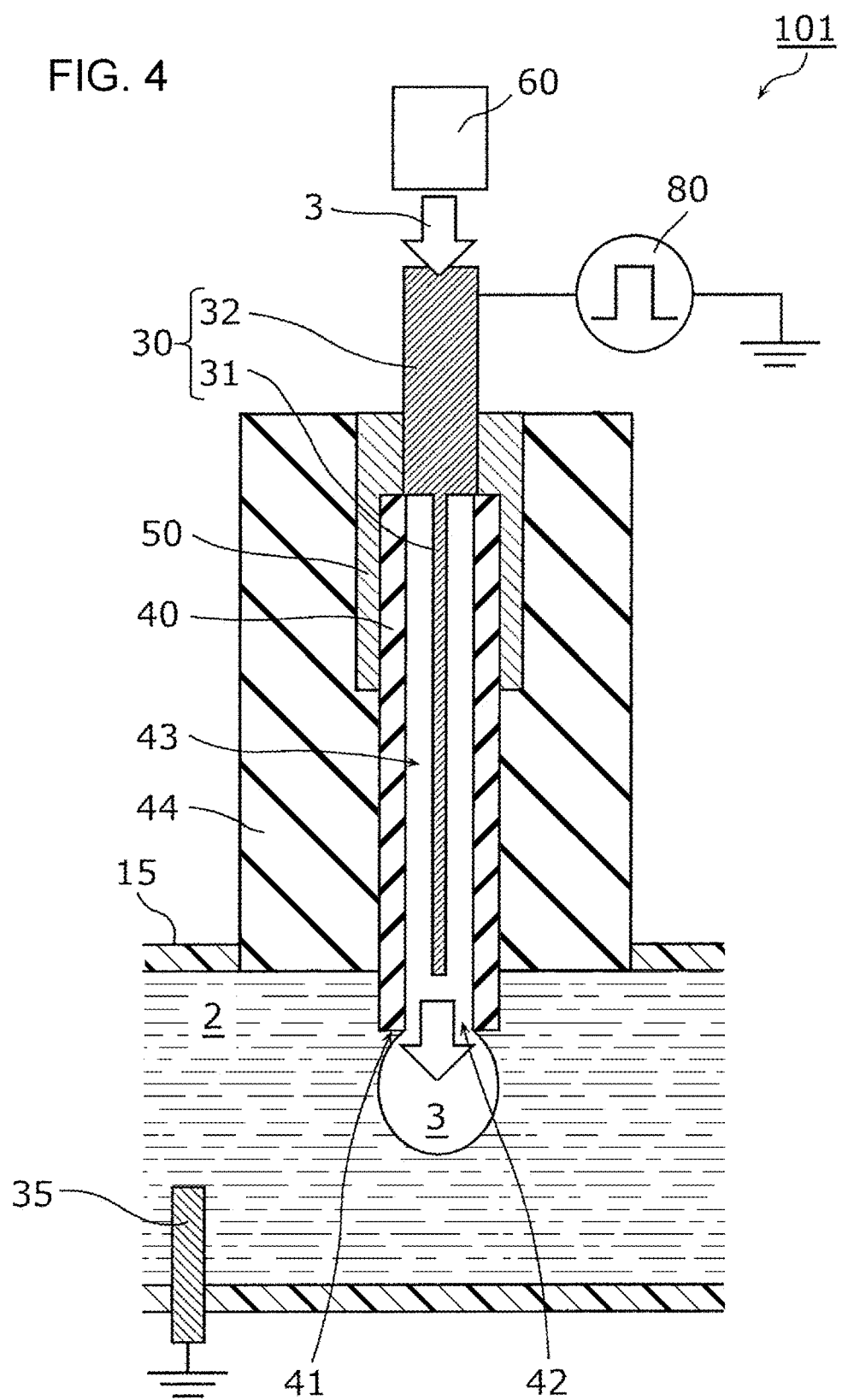
FIG. 4 is a cross-sectional view showing a configuration of the main components of a liquid processing apparatus according to Modification 1 to the embodiment.

FIG. 4 is a cross-sectional view showing a configuration of the main components of a liquid processing apparatus 101 according to Modification 1. As shown in FIG. 4, the liquid processing apparatus 101 according to Modification 1 differs from the liquid processing apparatus 100 according to the embodiment in that the liquid processing apparatus 101 further includes an insulator 44.

The insulator 44 is an example of a second insulator covering at least a part of the metallic member 50 so that the metallic member 50 does not touch the processed liquid 2. Specifically, the insulator 44 is located between the metallic member 50 and the processed liquid 2. The insulator 44 covers, for example, an end of the metallic member 50 that faces the front-end side. For example, as shown in FIG. 4, the insulator 44 covers the outer side face of the insulator 40, which is the first insulator, and the metallic member 50.

The insulator 44 is made of, for example, acrylic resin, vinyl chloride resin, or a similar material. However, this does not imply any limitation. For example, the insulator 44 may be made of the same material, e.g. alumina, as the insulator 40.

The shape of the insulator 40 is for example a circular cylinder but may alternatively be any shape such as a triangular cylinder or an elliptical cylinder. In Modification 1, the insulator 44 has an inner side face of a shape that is in conformance with the outer diameters of the metallic member 50 and the insulator 40. Specifically, the insulator 44 is in intimate contact with an outer side face of the metallic member 50 and an outer side face of the insulator 40 that is not covered with the metallic member 50.

This prevents the metallic member 50 and the processed liquid 2 from touching each other, thus making it possible to reduce the occurrence of a short circuit or a similar phenomenon. The unlikelihood of a short circuit makes it possible to reduce the occurrence of a failure in the liquid processing apparatus 101 and achieve stable discharge.

4-2. Modification 2

Figure 5:
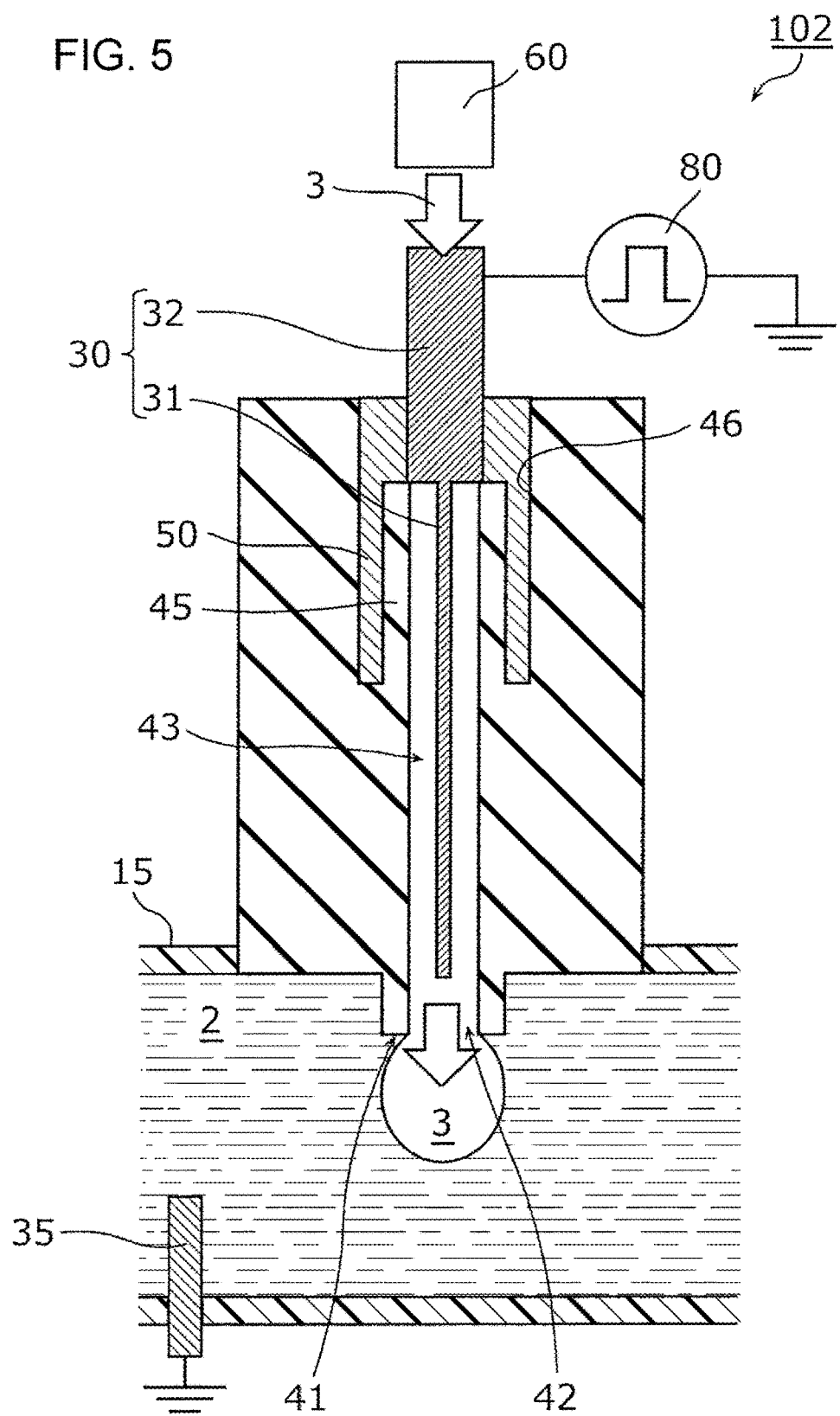
FIG. 5 is a cross-sectional view showing a configuration of the main components of a liquid processing apparatus according to Modification 2 to the embodiment.

FIG. 5 is a cross-sectional view showing a configuration of the main components of a liquid processing apparatus 102 according to Modification 2. As shown in FIG. 5, the liquid processing apparatus 102 according to Modification 2 differs from the liquid processing apparatus 100 according to the embodiment in that the liquid processing apparatus 102 includes an insulator 45 instead of including the insulator 40.

The insulator 45 is a combination of the insulator 40 according to the embodiment and the insulator 44 according to Modification 1. The insulator 45 is an example of the first insulator. In Modification 2, the metallic member 50 is buried in the insulator 45. That is, the insulator 45 is provided with a recess 46 in which the metallic member 50 is buried. The recess 46 is a recess formed in a cylindrical shape along the shape of the metallic member 50. The recess 46 may be formed in advance when the insulator 45 is formed or may be formed by performing cutting after the insulator 45 has been molded.

This prevents the metallic member 50 and the processed liquid 2 from touching each other, thus making it possible to reduce the occurrence of a short circuit or a similar phenomenon. The unlikelihood of a short circuit makes it possible to reduce the occurrence of a failure in the liquid processing apparatus 102 and achieve stable discharge.

4-3. Modification 3

Figure 6:
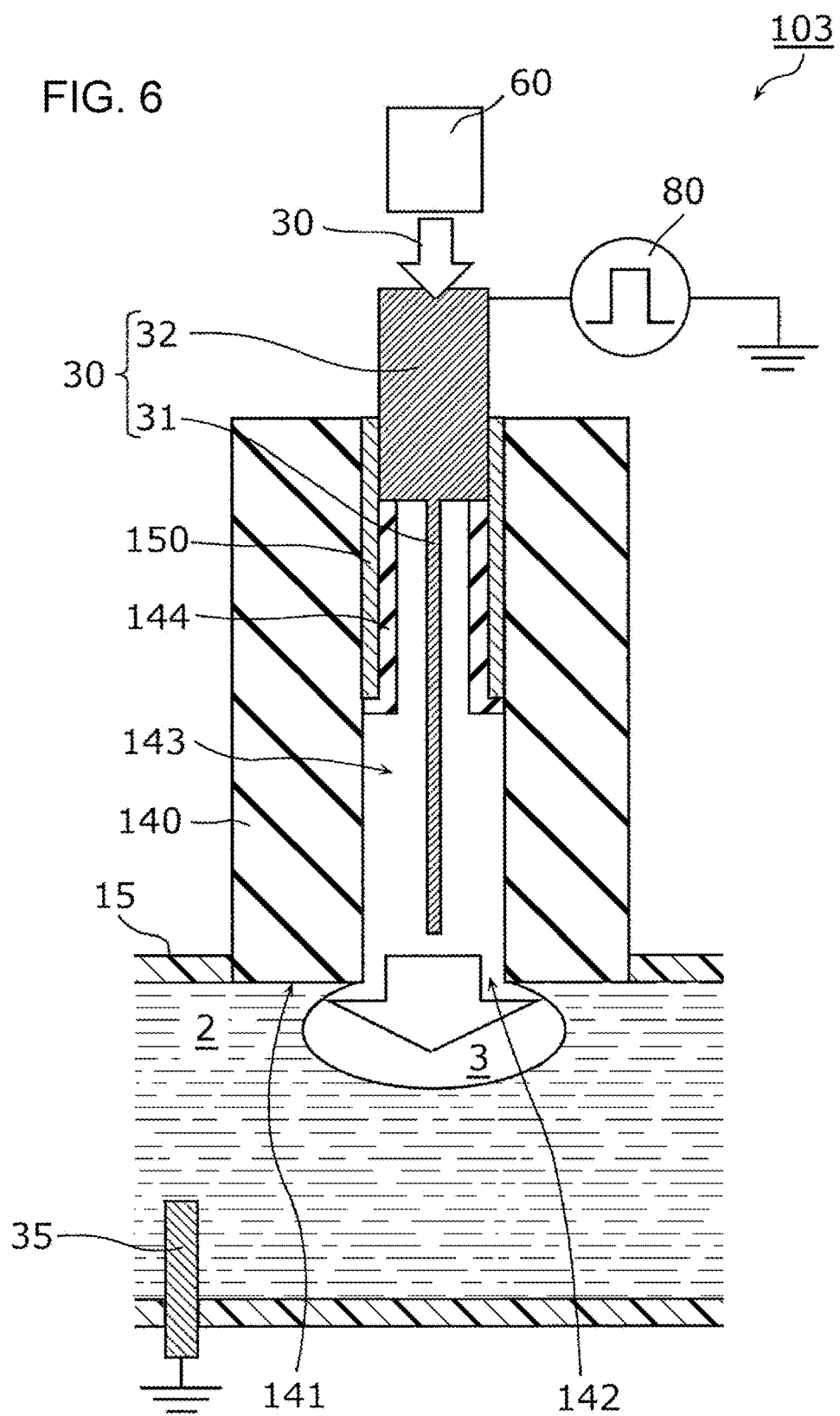
FIG. 6 is a cross-sectional view showing a configuration of the main components of a liquid processing apparatus according to Modification 3 to the embodiment.

FIG. 6 is a cross-sectional view showing a configuration of the main components of a liquid processing apparatus 103 according to Modification 3. As shown in FIG. 6, the liquid processing apparatus 103 according to Modification 3 differs from the liquid processing apparatus 100 according to the embodiment in that the liquid processing apparatus 103 includes an insulator 140 and an insulator 144 instead of including the insulator 40 and includes a metallic member 150 instead of including the metallic member 50. The insulators 140 and 144 are an example of the first insulator and correspond to a first portion and a second portion, respectively.

The metallic member 150 is disposed between the first electrode 30 and the insulator 140. That is, the metallic member 150 is disposed in a space 143 serving as an interior space of the insulator 140. For example, the metallic member 150 has a circular cylindrical shape whose inner diameter is substantially the same as the outer diameter of the supporting section 32 of the first electrode 30.

In Modification 3, the insulator 140 has an opening 142 formed in an end face 141 thereof, and this opening 142 is larger than the opening 42 of the insulator 40. That is, the space 143 is larger than the space 43. This provides a sufficient space in which to dispose the metallic member 150 and the insulator 144. It should be noted that since FIG. 6 is a mere example, the opening 142 may for example be the same in size as the opening 42.

The insulator 144 covers at least a part of the metallic member 150 so that the metallic member 150 is not exposed to the space 143. The insulator 144 is provided in order to prevent the processed liquid 2, which may enter the insulator 140, from touching the metallic member 150. For this purpose, the insulator 144 covers at least an end of the metallic member 150 that faces the front-end side.

The insulator 144 is formed in a cylindrical shape so as to surround the side face of the electrode section 31 of the first electrode 30. It should be noted that the insulator 144 may be in contact with the electrode section 31, provided at least a path of the gas 3 is ensured. The insulator 144 is made, for example, of an insulating resinous material. However, this does not imply any limitation.

This puts the metallic member 150 and the first electrode 30 at substantially the same potential, so that an electric field intensity inside the insulator 144 is substantially 0. This makes it possible to reduce Maxwell stress on the processed liquid 2. Modification 3 eliminates the need to provide an outer side of the insulator 140 with a metallic member and an insulator that protects the metallic member. This makes it possible to miniaturize the liquid processing apparatus 103 with a space-saving configuration.

4-4. Modification 4

Figure 7:
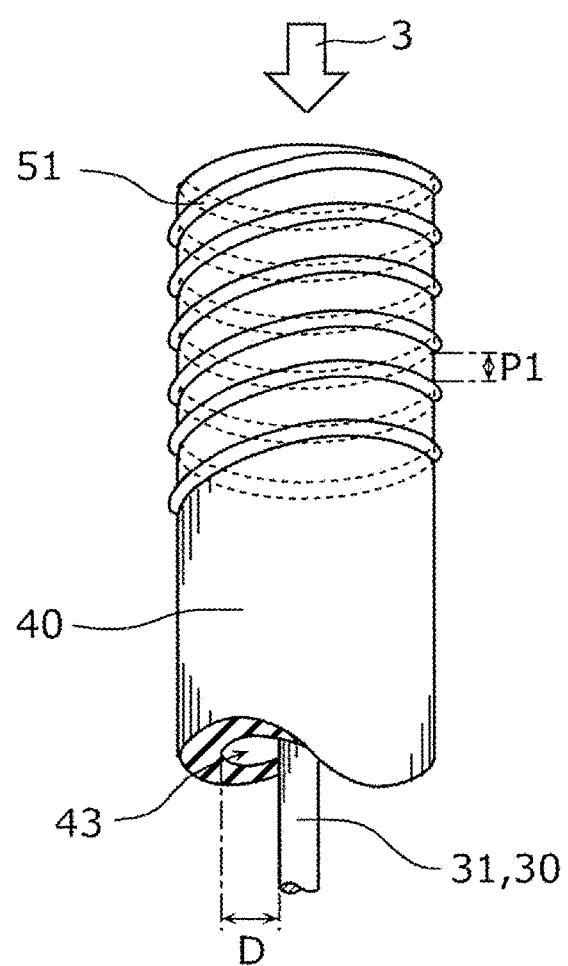
FIG. 7 is a perspective view showing the shape of a metallic member according to Modification 4 of the embodiment.

FIG. 7 is a perspective view showing the shape of a metallic member 51 according to Modification 4. As shown in FIG. 7, the metallic member 51 differs in shape from the metallic member 50 according to the embodiment.

Specifically, the metallic member 51 has a spiral shape. The spiral shape has a pitch P1 that is shorter than or equal to the distance between the insulator 40 and the first electrode 30.

Specifically, as shown in FIG. 7, the distance between the insulator 40 and the first electrode 30 is the distance D between an inner side face of the insulator 40 and an outer side face of the electrode section 31 and is equivalent to the width of the cylindrical space 43. An example of the distance D is, but is not limited to, 1 mm.

The spiral metallic member 51 needs only have such a thickness that leakage of an electric field does not take place. For example, the thickness of the metallic member 51 is greater than or equal to the pitch P1 of the spiral shape.

This makes it possible to use less of a metallic material as the metallic member 51 while keeping an electric field of substantially 0 inside the insulator 40, thus making it possible to reduce the weight of the metallic member 51. This in turn makes it possible to achieve reductions in weight and cost of the liquid processing apparatus 100.

4-5. Modification 5

Figure 8:
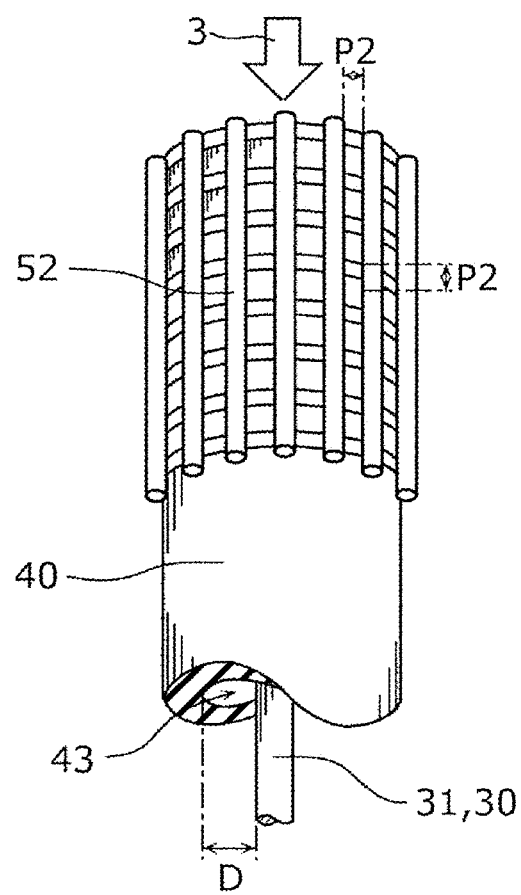
FIG. 8 is a perspective view showing the shape of a metallic member according to Modification 5 of the embodiment.

FIG. 8 is a perspective view showing the shape of a metallic member 52 according to Modification 5. As shown in FIG. 8, the metallic member 52 differs in shape from the metallic member 50 according to the embodiment.

Specifically, the metallic member 52 has a cylindrical mesh shape. The mesh shape has a mesh pitch P2 that is shorter than or equal to the distance between the insulator 40 and the first electrode 30. It should be noted that the mesh pitch P2 is the width of each opening of the mesh shape.

Although FIG. 8 shows an example in which the openings of the mesh shape are in a square shape, this does not imply any limitation. The openings may alternatively be in a rectangular shape, a diamond shape, or a similar shape.

Each line of the mesh metallic member 52 needs only have such a thickness that leakage of an electric field does not take place. For example, the thickness of each line of the metallic member 52 is greater than or equal to the mesh pitch P2.

This makes it possible to use less of a metallic material as the metallic member 52 while keeping an electric field of substantially 0 inside the insulator 40, thus making it possible to reduce the weight of the metallic member 52. This in turn makes it possible to achieve reductions in weight and cost of the liquid processing apparatus 100.

4-6. Modification 6

Figure 9:
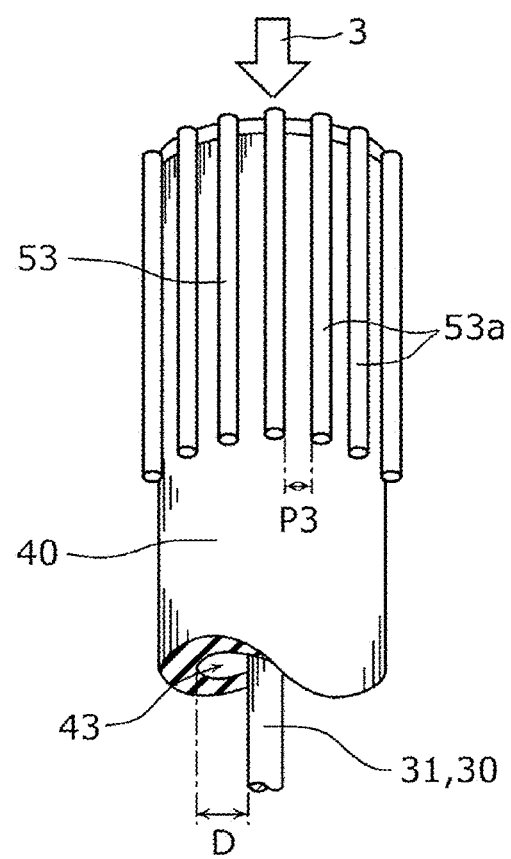
FIG. 9 is a perspective view showing the shape of a metallic member according to Modification 6 of the embodiment.

FIG. 9 is a perspective view showing the shape of a metallic member 53 according to Modification 6. As shown in FIG. 9, the metallic member 53 differs in shape from the metallic member 50 according to the embodiment.

Specifically, the metallic member 53 is shaped by a plurality of metallic rods 53a annularly arrayed at predetermined pitches P3. The predetermined pitches P3 are shorter than or equal to the distance between the insulator 40 and the first electrode 30. The plurality of metallic rods 53a are arrayed at regular pitches.

In Modification 6, each of the plurality of metallic rods 53a is a rod elongated in the direction in which the electrode section 31 of the first electrode 30 extends. Each of the plurality of metallic rods 53a has, for example, a circular columnar shape but may alternatively have a prismatic shape.

Each of the metallic rods 53a needs only have such a thickness that leakage of an electric field does not take place. For example, the thickness of each of the metallic rods 53a is greater than or equal to the predetermined pitches P3.

This makes it possible to use less of a metallic material as the metallic member 53 while keeping an electric field of substantially 0 inside the insulator 40, thus making it possible to reduce the weight of the metallic member 53. This in turn makes it possible to achieve reductions in weight and cost of the liquid processing apparatus 100.

4-7. Modification 7

Figure 10:
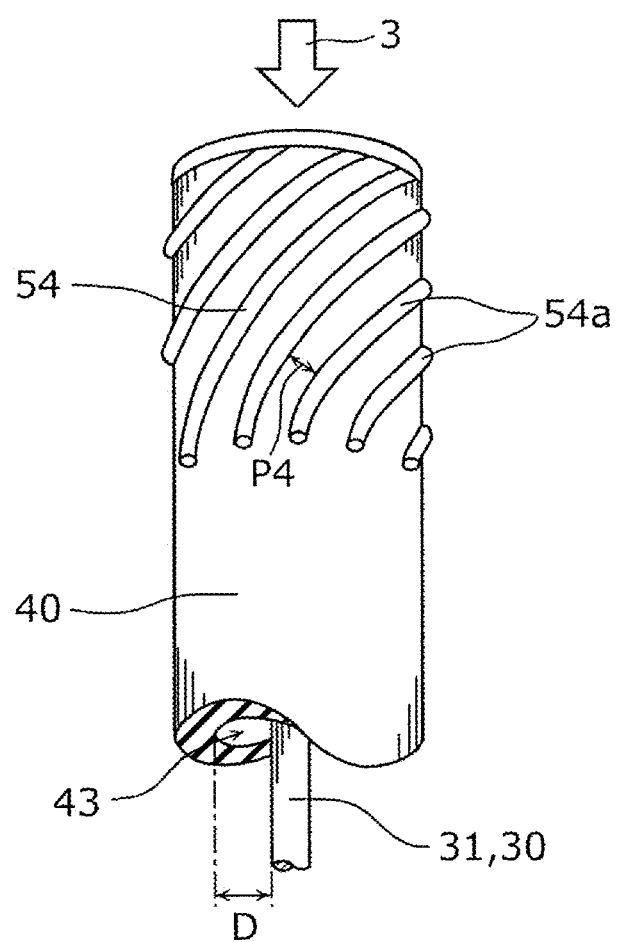
FIG. 10 is a perspective view showing the shape of a metallic member according to Modification 7 of the embodiment.

FIG. 10 is a perspective view showing the shape of a metallic member 54 according to Modification 7. As shown in FIG. 10, the metallic member 54 differs in shape from the metallic member 50 according to the embodiment.

Specifically, the metallic member 54 is shaped by a plurality of metallic rods 54a annularly arrayed at predetermined pitches P4. The predetermined pitches P4 are shorter than or equal to the distance between the insulator 40 and the first electrode 30. The plurality of metallic rods 54a are arrayed at regular pitches.

In Modification 7, each of the plurality of metallic rods 54a spirally extends along the outer side face of the insulator 40. This causes the metallic member 54 to form a multispiral structure. Each of the plurality of metallic rods 54a has, for example, a circular cross-sectional shape but may alternatively have a square, rectangular, or elliptical cross-sectional shape.

Each of the metallic rods 54a needs only have such a thickness that leakage of an electric field does not take place. For example, the thickness of each of the metallic rods 54a is greater than or equal to the predetermined pitches P4.

This makes it possible to use less of a metallic material as the metallic member 54 while keeping an electric field of substantially 0 inside the insulator 40, thus making it possible to reduce the weight of the metallic member 54. This in turn makes it possible to achieve reductions in weight and cost of the liquid processing apparatus 100.

5. Effects of Metallic Member

The following describes the effects that the liquid processing apparatus 100 according to the present embodiment brings about by including the metallic member 50. It should be noted that, although not described in detail, the aforementioned Modifications 1 to 7 bring about substantially the same effects.

First, a comparative example is described with reference to the case of an operation in the absence of the metallic member 50. A string electric potential gradient is present between the electrode section 31 and the insulator 40. This causes Maxwell stress that is proportional to the square of the electric field intensity to act on the processed liquid 2, so that the processed liquid 2 is drawn toward the back through the opening 42 of the insulator 40. In a case where the processed liquid 2 thus drawn approaches the back end of the space 43 of the insulator 40 and the voltage between the processed liquid 2 and the first electrode 30 exceeds the dielectric breakdown voltage, unwanted discharge occurs inside the insulator 40.

The occurrence of discharge causes an inorganic component such as calcium (Ca) or magnesium (Mg) contained in the processed liquid 2 to be deposited on the inner side face of the insulator 40. The deposition cases a problem such as a clogging of the space 43 of the insulator 40 or a further occurrence of unwanted discharge between the inorganic component thus deposited and the first electrode 30.

On the other hand, as mentioned above, the present embodiment makes it possible to prevent the entrance of the liquid under Maxwell stress by disposing the metallic member 50 on the outer perimeter of the insulator 40 and putting the metallic member 50 at the same potential as the first electrode 30. It should be noted that the same applies to a case such as Modification 3 where the metallic member 150 is disposed on the inner side of the insulator 140.

Figure 11A:
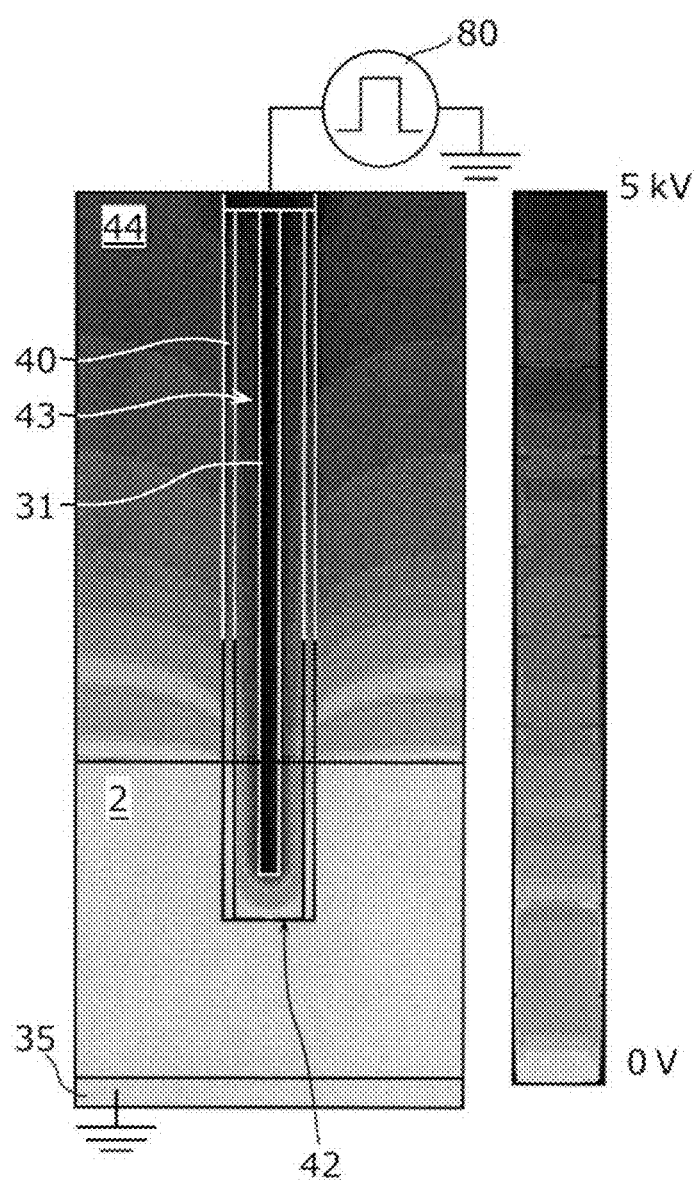
FIG. 11A is a diagram showing a result of an electric field simulation of a liquid processing apparatus according to a comparative example.
Figure 11B:
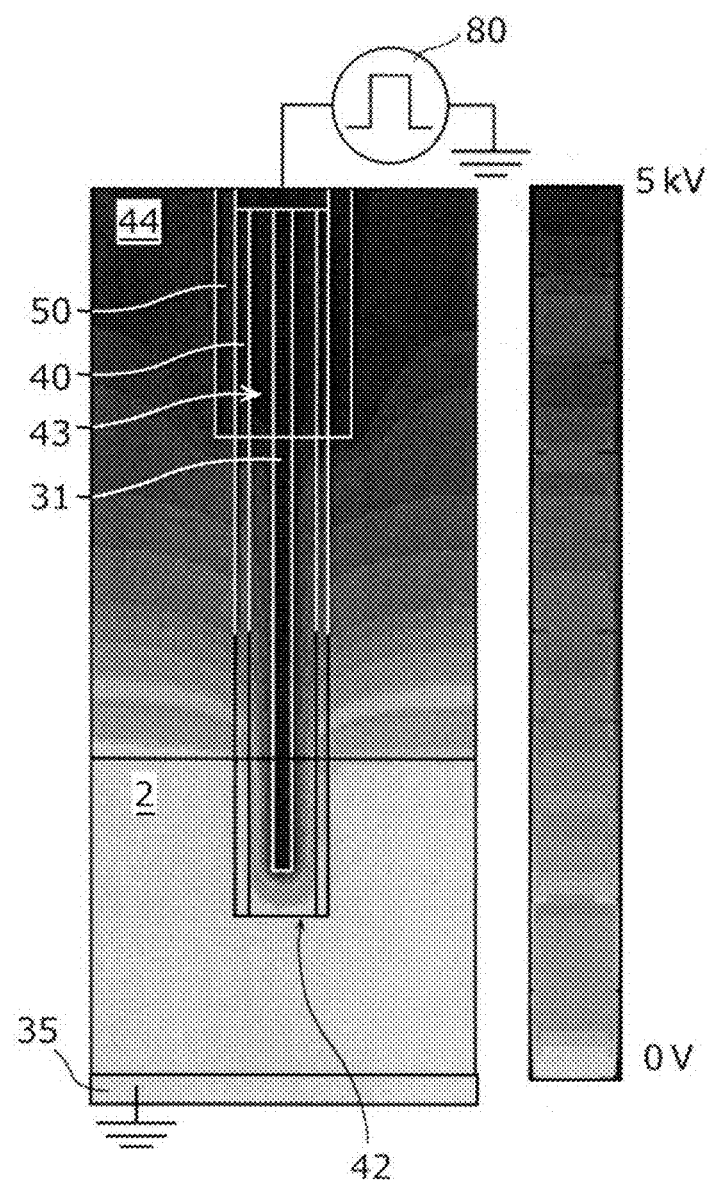
FIG. 11B is a diagram showing a result of an electric field simulation of the liquid processing apparatus according to Modification 1.

A more detailed description is given with reference to FIGS. 11A and 11B. FIGS. 11A and 11B are diagrams showing results of electric field simulations of the liquid processing apparatuses according to the comparative example and Modification 1, respectively. Specifically, FIG. 11A shows an electric potential distribution in a case where the metallic member 50 is disposed on the outer perimeter of the insulator 40. FIG. 11B shows an electric potential distribution in the presence of the application of the same potential to the metallic member 50 as the first electrode 30 in a case where the metallic member 50 is disposed on the outer perimeter of the insulator 40 and, as in Modification 1, the insulator 44 covering the metallic member 50 is provided.

In either case, it was assumed that a voltage of 5 kV is applied to the first electrode 30 and the processed liquid 2 is a perfect conductor connected to a ground potential. Further, alumina was selected as the insulator 40. Acrylic resin was selected as the insulator 44 to hold the insulator 40. Air at room temperature under atmospheric pressures was selected as the gas 3. The dielectric constant of each of the constituent elements was used as a parameter.

According to these results, in a case such as that shown in FIG. 11A where the metallic member 50 is not disposed, an electric potential gradient is found between the electrode 31 and the inner side face of the insulator 40 in the space 43 in the insulator 40. This means that a strong electric field is generated from the electrode section 31 toward the insulator 40. This shows, in view of the application of Maxwell stress that is proportional to the square of the electric field intensity, that the liquid enters the insulator 40.

Meanwhile, in a case such as that shown in FIG. 11B where the metallic member 50 is disposed, no electric potential gradient is found particularly in a region surrounded by the metallic member 50. This shows that the electric field between the electrode section 31 and the insulator 40 is eliminated and generation of Maxwell stress can be reduced. Therefore, the entrance of the liquid into the insulator 40 can be prevented.

In this way, the liquid processing apparatuses according to the present embodiment and the modifications make it possible to prevent the entrance of the processed liquid 2 into a back part of the insulator 40. This makes it possible to suppress unwanted discharge in the back part of the insulator 40. This in turn makes it possible to prevent a decrease in discharge efficiency in the vicinity of the opening 42 from occurring due to discharge in the back part of the insulator 40. This also makes it possible to prevent a member holding the insulator 40 or a similar member from burning out due to discharge in the back part of the insulator 40. This makes it possible to maintain the performance of the liquid processing apparatuses over a long period of time and contribute to safety and security.

Other Embodiments

Although the foregoing has described a liquid processing apparatus according to one or more aspects with reference to embodiments, the present disclosure is not limited to these embodiments. Embodiments based on the application to the present embodiment of various modifications conceived of by persons skilled in the art and embodiments based on combinations of constituent elements of different embodiments are encompassed in the scope of the present disclosure, provided such embodiments do not depart from the spirit of the present disclosure.

For example, although the forgoing embodiment generates plasma in the gas 3 by supplying the gas 3 into the processed liquid 2 while the processed liquid 2 is flowing by circulating. For example, the processed liquid 2 may be a liquid that is not flowing or, specifically, still water. In this case, the liquid processing apparatus 100 does not need to include the processing tank 10, the piping unit 20, and the liquid supply device 70.

Further, for example, although an example has been shown in which the first electrode 30 includes the electrode section 31 and the supporting section 32, the first electrode 30 may alternatively be a single rod-shaped (circular columnar) electrode. Alternatively, the first electrode 30 may be a prismatic or plate electrode. he same applies to the second electrode 35. Further, for example, a plurality of the first electrodes 30, a plurality of the insulators 40, and a plurality of the metallic members 50 may be provided.

Further, each of the embodiments described above is subject to various changes, substitutions, additions, omissions, and the like within the scope of the claims or the scope of equivalents thereof.

What is claimed is:
1. A liquid processing apparatus comprising:
 a container for holding liquid;
 a first electrode at least a part of which is disposed in the liquid;
 a second electrode at least a part of which is disposed in the liquid;
 a first insulator that has a cylindrical shape and at least partly surrounds a side face of the first electrode via a space, the first insulator having an opening in an end face of the first insulator;
 a gas supply device that supplies gas into the space and releases the gas into the liquid via the opening;
 a power source that applies a voltage between the first electrode and the second electrode and generates plasma; and
 a metallic member that partly surrounds the side face of the first electrode via the space, wherein
 the metallic member is electrically connected to the first electrode, and
 at least a part of the first insulator is disposed between the first electrode and the metallic member.
2. The liquid processing apparatus according to claim 1, wherein
 the first electrode has a first end and a second end located closer to the opening than the first end, and the metallic member does not surround a portion of the side face of the first electrode, the portion extending from the second end to a position between the first end and the second end.

3. The liquid processing apparatus according to claim 1, wherein
   a part of the first electrode surrounded by the space has two ends,
   one end of the two ends is located farther away from the opening than the other end of the two ends, and
   the metallic member surrounds a portion of the side face of the first electrode, the portion extending from the one end to a position that is located at a distance of 10 mm or longer from the one end.

4. The liquid processing apparatus according to claim 1, wherein a potential of the metallic member becomes substantially the same as a potential of the first electrode when the voltage is applied between the first electrode and the second electrode.

5. The liquid processing apparatus according to claim 1, wherein the metallic member is in contact with an outer side face of the first insulator.

6. The liquid processing apparatus according to claim 5, further comprising a second insulator covering at least a part of the metallic member.

7. The liquid processing apparatus according to claim 1, wherein the metallic member is buried in the first insulator.

8. The liquid processing apparatus according to claim 1, wherein
   the first insulator includes a first portion and a second portion,
   the metallic member is disposed between the first portion and the second portion, and
   the second portion is disposed between the metallic member and the first electrode.

9. The liquid processing apparatus according to claim 8, wherein the first and second portions of the first insulator are made of different materials from each other.

10. The liquid processing apparatus according to claim 8, wherein the first and second portions of the first insulator are made of the same material.

11. The liquid processing apparatus according to claim 1, wherein the metallic member has a cylindrical shape.

12. The liquid processing apparatus according to claim 1, wherein the metallic member has a cylindrical mesh shape.

13. The liquid processing apparatus according to claim 12, wherein the cylindrical mesh shape has openings whose widths are shorter than or equal to a distance between the first insulator and the first electrode.

14. The liquid processing apparatus according to claim 1, wherein the metallic member has a spiral shape.

15. The liquid processing apparatus according to claim 14, wherein the spiral shape has spirals placed at pitches that are shorter than or equal to a distance between the first insulator and the first electrode.

16. The liquid processing apparatus according to claim 1, wherein the metallic member has a shape of a plurality of metallic rods annularly arrayed at pitches.

17. The liquid processing apparatus according to claim 16, wherein the pitches are shorter than or equal to a distance between the first insulator and the first electrode.

18. The liquid processing apparatus according to claim 1, wherein
   the first electrode includes an electrode section having a circular columnar shape,
   the first insulator is a circular cylinder surrounding a part of a side face of the electrode section, and
   the electrode section and the first insulator are coaxially disposed.

* * * * *